United States Patent [19]

Szczepanski et al.

[11] Patent Number: 4,758,667
[45] Date of Patent: Jul. 19, 1988

[54] PROCESS FOR THE PREPARATION OF 2-(IMIDAZOLIN-2-YL)-3-PYRIDINE- AND -3-QUINOLINECARBOXYLIC ACIDS

[75] Inventors: Henry Szczepanski, Wallbach; Dieter Dürr, Bottmingen, both of Switzerland

[73] Assignee: Ciba-Geigy Corporation, Ardsley, N.Y.

[21] Appl. No.: 11,077

[22] Filed: Feb. 5, 1987

[30] Foreign Application Priority Data

Feb. 10, 1986 [CH] Switzerland ............... 515/86

[51] Int. Cl.$^4$ ........................................... C07D 401/02
[52] U.S. Cl. ..................................... 546/167; 546/278
[58] Field of Search ................. 546/167, 278; 548/337

[56] References Cited

U.S. PATENT DOCUMENTS 4,518,780  5/1985  Barton et al. ................... 546/167
4,562,257 12/1985  Petrocine ......................... 546/169
4,638,068  1/1987  Los .................................. 546/169

FOREIGN PATENT DOCUMENTS 41623 12/1981 European Pat. Off. .

Primary Examiner—Glennon H. Hollrah
Assistant Examiner—D. B. Springer
Attorney, Agent, or Firm—Kevin T. Mansfield; Edward M. Roberts

[57] ABSTRACT

There is disclosed a process for the preparation of 2-(imidazolin-2-yl)-3-pyridine and -3-quinolinecarboxylic acids of formula

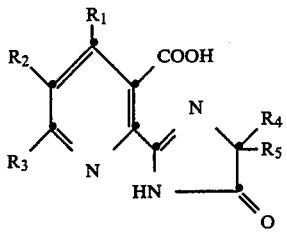

wherein $R_1$ is hydrogen or $C_1$–$C_4$alkyl, $R_2$ is hydrogen, halogen, $C_1$–$C_4$alkyl, $C_1$–$C_4$hydroxyalkyl, $C_1$–$C_4$alkoxy, phenyl or phenyl-$C_1$–$C_4$alkyl, or phenyl or phenyl-$C_1$–$C_4$-alkyl, each substituted by one $C_1$–$C_4$alkyl, $C_1$–$C_4$alkoxy or halogen, $R_3$ is hydrogen, $C_1$–$C_4$alkyl, phenyl, phenyl-$C_1$–$C_4$-alkyl, or phenyl or phenyl-$C_1$–$C_4$-alkyl, each substituted by one $C_1$–$C_4$alkyl, $C_1$–$C_4$alkoxy or halogen, $R_2$ and $R_3$ together are 1,3-butadienylene which can be substituted by halogen, $C_1$–$C_4$alkyl, $C_1$–$C_4$alkoxy, $C_1$–$C_4$ haloalkyl, $C_1$–$C_4$alkylsulfonyl, nitro, cyano, phenyl, phenoxy, or phenyl or phenoxy, each substituted by one $C_1$–$C_4$alkyl, $C_1$–$C_4$alkoxy or halogen, and $R_4$ and $R_5$ are each independently of the other $C_1$–$C_4$alkyl. In this process, the 2-(imidazolin-2-yl)-3-pyridine- and -3-quinolinecarboxylic acids of the above formula are obtained by reacting a 2,3-pyridine- or 2,3-quinolinedidicarboxylic acid ester of formula

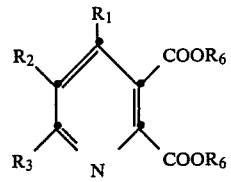

wherein $R_1$, and $R_2$ and $R_3$ are as defined above and $R_6$ is $C_1$–$C_8$alkyl, phenyl or $C_1$–$C_4$phenylalkyl with a 2-aminoalkanecarboxamide of formula

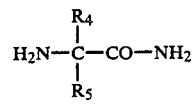

wherein $R_4$ and $R_5$ are as defined above, in an inert solvent and in the presence of a strong base, direct to a salt of a 2-(imidazolin-2-yl)-3-pyridine- or -3-quinolinecarboxylic acid of the above formula, from which the free 2-(imidazolin-2-yl)-3-pyridine- or -3-quinolinecarboxylic acids of the above formula are obtained by converting said salt into an aqueous solution and adding an acid. The 2-(imidazolin-2-yl)-3-pyridine- and -3-quinolinecarboxylic acids of the above formula have herbicidal properties and can be used for controlling undesired plant growth.

15 Claims, No Drawings

PROCESS FOR THE PREPARATION OF 2-(IMIDAZOLIN-2-YL)-3-PYRIDINE- AND -3-QUINOLINECARBOXYLIC ACIDS

The present invention relates to a process for the preparation of 2-(imidazolin-2-yl)-3-pyridine- and -3-quinolinecarboxylic acids of formula I

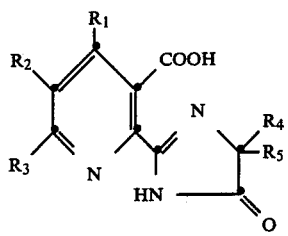

wherein $R_1$ is hydrogen or $C_1$–$C_4$alkyl, $R_2$ is hydrogen, halogen, $C_1$–$C_4$alkyl, $C_1$–$C_4$hydroxyalkyl, $C_1$–$C_4$alkoxy, phenyl or phenyl-$C_1$–$C_4$-alkyl, or phenyl or phenyl-$C_1$–$C_4$-alkyl, each substituted by one $C_1$–$C_4$alkyl, $C_1$–$C_4$alkoxy or halogen, $R_3$ is hydrogen, $C_1$–$C_4$alkyl, phenyl, phenyl-$C_1$–$C_4$-alkyl, or phenyl or phenyl-$C_1$–$C_4$-alkyl, each substituted by one $C_1$–$C_4$alkyl, $C_1$–$C_4$alkoxy or halogen, $R_2$ and $R_3$ together are 1,3-butadienylene which can be substituted by halogen, $C_1$–$C_4$alkyl, $C_1$–$C_4$alkoxy, $C_1$–$C_4$haloalkyl, $C_1$–$C_4$alkylsulfonyl, nitro, cyano, phenyl, phenoxy, or phenyl or phenoxy, each substituted by one $C_1$–$C_4$alkyl, $C_1$–$C_4$alkoxy or halogen, and $R_4$ and $R_5$ are each independently of the other $C_1$–$C_4$alkyl.

The compounds of formula I have herbicidal properties and can be used for controlling undesired plant growth. Compounds of this kind are disclosed e.g. in published European patent application No. 0 041 623 and in U.S. Pat. No. 4,518,780.

Published European patent application No. 0 041 623 discloses the preparation of 2-(imidazolin-2-yl)-3-pyridine- and -3-quinolinecarboxylic acids, starting from derivatives of the corresponding 2,3-pyridine- and 2,3-quinolinedicarboxylic acids and 2-aminoalkanecarboxylic acid derivatives. The derivatives of 2,3-pyridine- and 2,3-quinolinedicarboxylic acids referred to in this publication are the monoesters and the acid halides thereof, the monoamides and, in particular, the anhydrides; and the 2-aminoalkanecarboxylic acid derivatives mentioned are the free carboxylic acids, the amides and, in particular, the nitriles. Thus, for example, 2-(5-isopropyl-5-methyl-4-oxoimidazolin-2-yl)-3-pyridinecarboxylic acid can be prepared in a yield of c. 32% of theory, based on the anhydride employed, starting from 2,3-pyridinedicarboxylic anhydride and 2-amino-2,3-dimethylbutyronitrile in accordance with the process steps described in Examples 1, 2 and 6 of the above mentioned European patent application. The preparation of the same compound, starting from 2,3-pyridinedicarboxylic anhydride and 2-amino-2,3-dimethylbutyramide, in a yield of 63% of theory, based on the anhydride employed, is described in U.S. Pat. No. 4,518,780. This process is carried out by reacting the anhydride and the aminobutyramide first in acetonitrile to give a mixture of isomeric 2,3-pyridinedicarboxylic monoamides, removing the solvent, treating the residue at 80° C. with aqueous sodium hydroxide solution, and separating the product by addition of acid. By means of the same method, 2-(5-isopropyl-5-methyl-4-oxoimidazolin-2-yl)-6-isopropyl-3-pyridinecarboxylic acid is obtained in a yield of 51% of theory, and 2-(5-isopropyl-5-methyl-5-oxoimidazolin-2-yl)-3-quinolinecarboxylic acid in a yield of 50% of theory, said yields being based in each case on the anhydride employed.

The starting anhydrides in both known processes are highly reactive compounds which, on account of their sensitivity to moisture, can only be transported and stored by maintaining certain safety precautions. The process itself comprises two separate reaction steps and is therefore fairly complicated. Further, the process is also unsatisfactory as regards the yields obtained.

Accordingly, it is the object of the present invention to provide a process for the preparation of 2-(2-imidazolin-2-yl)-3-pyridine- and -3-quinolinecarboxylic acids of formula I, starting from readily available starting materials, which process makes it possible to prepare these compounds in simple manner and in good yield.

Specifically, the invention relates to a process for the preparation of 2-(imidazolin-2-yl)-3-pyridine- and -3-quinolinecarboxylic acids of formula I, which comprises reacting a 2,3-pyridine- or 2,3-quinolinedicarboxylic acid ester of formula II

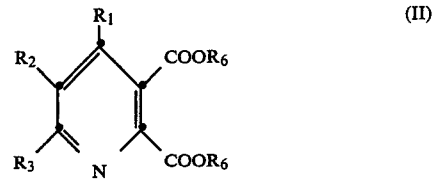

wherein $R_1$, $R_2$ and $R_3$ are as defined for formula I, and $R_6$ is $C_1$–$C_8$alkyl, phenyl or $C_1$–$C_4$phenylalkyl, with a 2-aminoalkanecarboxamide of formula III

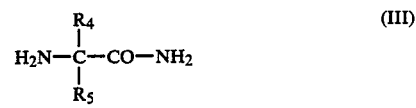

wherein $R_4$ and $R_5$ are as defined for formula I, in the presence of a strong base and at a temperature in the range from room temperature to the reflux temperature of the reaction mixture, dissolving the resultant salt of 2-(imidazolin-2-yl)-3-pyridine- or -3-quinolinecarboxylic acid of formula I in water, adjusting the pH of the aqueous solution to 1.5–4.5, and isolating the free 2-(imidazolin-2-yl)-3-pyridine- or -3-quinolinecarboxylic acid of formula I.

Examples of suitable inert solvents are liquid aromatic hydrocarbons and halogenated hydrocarbons such as benzene, toluene, chlorobenzenes and xylenes, $C_1$–$C_{10}$alkanols, preferably $C_1$–$C_4$alkanols such as methanol, ethanol, propanol, isopropanol, n-butanol, sec-butanol, tert-butanol and isobutanol, ethereal compounds such as tetrahydrofuran and dioxane, as well as strongly polar solvents such as acetonitrile, N,N-dimethylformamide and dimethylsulfoxide. It is advantageous to use water-immiscible solvents such as benzene, toluene, chlorobenzene or xylenes. Suitable strong bases in the presence of which the reaction of a 2,3-pyridine- or 2,3-quinolinedicarboxylic acid ester of formula II with a 2-aminoalkanecarboxamide of formula III is carried out are alkali metal hydroxides and alkali metal alcoholates. Preferred bases are alkali metal alcoholates, especially those derived from $C_1$–$C_4$alkaknols, and are e.g. sodium methylate, sodium ethylate, sodium isopropylate and potassium tert-butylate. If alkanols are used as inert solvents, particularly suitable bases are alkali metal hydroxides such as sodium hydroxide and potassium hydroxide. The reaction can also be carried out in the presence of potassium carbonate in ethanol. An at least equimolar amount of strong base will normally be used, based on the 2,3-pyridine- or 2,3-quinolinedicarboxylic acid ester of formula I. In carrying out the process of this invention, it has proved expedient to use from 1 to 3 moles of base per mole of 2,3-pyridine- or 2,3-quinolinedicarboxylic acid ester of formula II. It is preferred to use from 1.5 to 2.5 moles of base per mole of 2,3-pyridine- or 2,3-quinolinedicarboxylic acid ester of formula II.

Within the indicated range from room temperature to the reflux temperature of the reaction mixture, the preferred temperature range for carrying out the process of the invention is from 50°–90° C.

Different methods may be employed for dissolving the directly obtained salt of a 2-(imidazolin-2-yl)-3-pyridine- or -3-quinolinecarboxylic acid of formula I, depending on the solvent employed and taking into account the solubility of the salt in the respective solvent. The salt normally precipitates almost completely from the reaction mixture, especially when using a liquid aromatic hydrocarbon or a halogenated hydrocarbon such as toluene or chlorobenzene. The salt can then be isolated by filtration and dissolved in water or else converted into an aqueous solution direct by extraction with water. If the solvent is an alkanol, especially a lower alkanol such as methanol, ethanol or isopropanol, the reaction mixture can be diluted direct with water and further worked up. This also applies to the use of tetrahydrofuran, dioxane, acetonitrile, dimethylformamide or dimethylsulfoxide. However, it is also possible to remove the solvent entirely or partially by distillation and to take up the residue in water.

The 2-(imidazolin-2-yl)-3-pyridine- and -3-quinolinecarboxylic acids of formula I are precipitated from the aqueous solution of their salts by adjusting the pH of the aqueous solution to 1.5 to 4.5, preferably to 3 to 4, by addition of an acid. Suitable acids are mineral acids, such as hydrochloric acid, sulfuric acid and phosphoric acid, as well as organic acids such as formic acid and acetic acid, or halogenated acetic acids such as chloroacetic acid. It is preferred to effect the precipitation of the salts of 2-(imidazolin-2-yl)pyridine- and -3-quinolinecarboxylic acids of formula I with hydrochloric acid or sulfuric acid.

The free 2-(imidazolin-2-yl)-3-pyridine- and -3-quinolinecarboxylic acids of formula I precipitated from the aqueous solutions of their salts by addition of acid can normally be isolated by filtration or centrifugation. However, it is also possible to isolate the free 2-(imidazolin-2-yl)-pyridin- or quinoline-3-carboxylic acids by extraction with a water-immiscible solvent, e.g. a halogenated hydrocarbon such as methylene chloride, chloroform or carbon tetrachloride, and by subsequent evaporation of the solvent. This method is particularly expedient if the free 2-(imidazolin-2-yl)-3-pyridine- and -3-quinolinecarboxylic acids of formula I cannot be precipitated, or can only be incompletely precipitated, from the aqueous solution of their salts. This method is also expedient if the aqueous solution of the salts of the 2-(imidazolin-2-yl)-3-pyridine- and 3-quinolinecarboxylic acids of formula I contains a water-immiscible solvent such as a lower alkanol, tetrahydrofuran, dioxane, dimethylformamide or dimethylsulfoxide, which is able to increase the solubility of the free acids in aqueous medium.

Preferred 2-(imidazolin-2-yl)-3-pyridine- and -3-quinolinecarboxylic acids of formula I which can be obtained by the process of this invention are those in which $R_1$ is hydrogen, $R_2$ and $R_3$ are each independently of the other hydrogen, $C_1$–$C_2$alkyl, $C_1$–$C_2$haloalkyl, $C_1$–$C_2$alkoxy or halogen, and $R_2$ and $R_3$ together are 1,3-butadienylene, and $R_4$ and $R_5$ are each independently of the other $C_1$–$C_3$alkyl.

Particularly preferred 2-(imidazolin-2-yl)-3-pyridine- and -3-quinolinecarboxylic acids of formula I are those in which $R_1$ is hydrogen, $R_2$ and $R_3$ are each independently of the other $C_1$–$C_2$alkyl or halogen and together are 1,3-butadienylene, $R_4$ is methyl and $R_5$ is isopropyl.

The $C_1$–$C_4$alkyl moieties of the substituents $R_1$ to $R_5$ may be straight chain or branched and comprise methyl, ethyl, n-propyl, isopropyl, n-butyl, sec-butyl, isobutyl and tert-butyl. This also applies to alkyl moieties substituted by halogen or phenyl. The phenyl moieties of substituents $R_1$ to $R_5$ can be monosubstituted by halogen, $C_1$–$C_4$alkyl or $C_1$–$C_4$haloalkyl.

A preferred embodiment of the process of this invention comprises carrying out the reaction of a 2,3-pyridine- or 2,3-quinolinedicarboxylic acid ester of formula II with a 2-aminoalkanecarboxamide of formula III in the presence of 1.5 to 2.5 moles of an alkali metal alcoholate per mole of diester of formula II, at a temperature in the range from 50° to 90° C., and in a liquid aromatic hydrocarbon or halogenated hydrocarbon, converting the isolated salt of the resultant 2-(imidazolin-2-yl)-3-pyridine-or -3-quinolinecarboxylic acid of formula I into an aqueous solution by addition of water, separating the organic phase, adjusting the pH of the aqueous phase to 3–4 by addition of aqueous hydrochloric acid or aqueous sulfuric acid, and isolating the free 2-(imidazolin-2-yl)-3-pyridine or -3-quinolinecarboxylic acid of formula I.

The starting 2,3-pyridinedicarboxylic acid esters of formula II can be obtained in simple manner by esterification of 2,3-pyridinedicarboxylic acid with appropriate alcohols. The 2,3-pyridinedicarboxylic acid can in turn be obtained by oxidation of quinoline (q.v. German patent specification No. 1 010 524 and U.S. Pat. No. 2,512,482). Further, the 2,3-pyridinedicarboxylic acid esters of formula II can be obtained by the methods described in published European patent applications Nos. 0 161 221 and 0 172 140, starting from a hydrazone of an $\alpha,\beta$-unsaturated carbonyl compound and a maleic acid derivative by means of a Diels-Alder reaction. The 2,3-quinolinedicarboxylic acid esters of formula II can be obtained by the method described in J. Org. Chem. 49, 4999–5000, 1984. The 2-aminoalkanecarboxamides of formula II are for the most part known compounds which can be obtained in known manner by reacting appropriate ketones with ammonia and hydrocyanic acid.

The process of this invention makes it possible to prepare the 2-imidazolin-2-yl)-3-pyridine- and -3-quinolinecarboxylic acids of formula I from starting materials which are readily accessible and easy to handle in simple manner and in good yield. In contradistinction to the prior art processes, the salts of the 2-(imidazolin-2-yl)-3-pyridine- and -3-quinolinecarboxylic acids of formula I are obtained in one reaction step. A further advantage of the process of this invention is that the desired 2-(imidazolin-2-yl)-3-pyridine- and -3- quinolinecarboxylic acids of formula I are obtained in pure form free from isomeric 3-(imidazolin-2-yl)-2-pyridine- and -2-quinolinecarboxylic acids.

The following examples illustrate the process of the invention in more detail.

EXAMPLE 1

Preparation of 2-(5-isopropyl-5-methyl-4-oxoimidazolin-2-yl)-3-pyridinecarboxylic acid 141.5 g (0.636 mole) of diethyl 2,3-pyridinedicarboxylate and 82.8 g (0.636 mole) of 2-amino-2,3-dimethylbutyramide are dissolved in 300 ml of toluene. With stirring, 160 g (1.4 moles) of potassium tert-butylate are then added in portions, whereupon the temperature of the reaction mixture rises to 50°–60° C. When the addition of potassium tert-butylate is complete, the reaction mixture is stirred for 3 hours at 80° C., then cooled to room temperature, and the potassium salt of 2-(5-isopropyl-5-methyl-4-oxoimidazolin-2-yl)-3-pyridinecarboxylic acid is isolated by filtration, washed with 3×100 ml of ether, and dissolved in water. The aqueous solution of the potassium salt is adjusted to pH 4 with 37% hydrochloric acid, whereupon the free 2-(5-isopropyl-5-methyl-4-oxoimidazolin-2-yl)-3-pyridinecarboxlyic acid precipitates. The product is isolated by filtration and dissolved in methylene chloride. The filtrate is extracted with methylene chloride and the extract is combined with the solution of the product in methylene chloride. The combined methylene chloride solutions are dried over magnesium sulfate and the solvent is removed by distillation, affording 132.8 g (80% of theory) of 2-(5-isopropyl-5-methyl-4-oxoimidazolin-2-yl)-3-pyridinecarboxylic acid of m.p. 167°–169° C.

EXAMPLE 2

Preparation of 2-(5-isopropyl-5-methyl-4-oxoimidazolin-2-yl)-5-methyl-3-pyridinecarboxylic acid With stirring, 116 g (1.034 moles) of potassium tert-butylate are added in portions to a solution of 123 g (0.519 mole) of diethyl 5-methyl-2,3-pyridinedicarboxylate and 67.5 g (0.519 mole) of 2-amino-2,4-dimethylbutyramide in 600 ml of toluene. During the addition of potassium tert-butylate the mixture exotherms to 60° C. When the addition of potassium tert-butylate is complete, the reaction mixture is heated to 80° C. and stirred overnight. Then 800 ml of water are added to the mixture which has cooled to room temperature, and the layers are separated. The aqueous phase is adjusted to pH 3 by addition of 85 ml of 37% hydrochloric acid, cooled to 0° C. and filtered. The product is dried, affording 97.8 g (69% of theory) of 2-(5-isopropyl-5-methyl-4-oxoimidazolin-2-yl)-5-methyl-3-pyridinecarboxylic acid of m.p. 200°–202° C.

EXAMPLE 3

Preparation of 2-(5-isopropyl-5-methyl-4-oxoimidazolin-2-yl)-6-methyl-3-pyridinecarboxylic acid With stirring, 45 g (0.4 mole) of potassium tert-butylate are added at room temperature to a solution of 41.8 g (0.2 mole) of dimethyl 6-methyl-2,3-pyridinedicarboxylate and 26.6 g (0.2 mole) of 2-amino-2,3-dimethylbutyramide in 600 ml of toluene. When the addition of potassium tert-butylate is complete, the reaction mixture is heated to 90° C. and stirred for 4 hours at this temperature. The reaction mixture is then cooled to room temperature and the potassium salt of 2-(5-isopropyl-5-methyl-4-oxoimidazolin-2-yl)-6-methyl-3-pyridinecarboxylic acid is isolated by filtration and dried. The potassium salt is then dissolved in water and the pH of the solution is adjusted to 3 by addition of 37% hydrochloric acid. The resultant clear solution is extracted once with diethyl ether and twice with methylene chloride. The combined extracts are dried over magnesium sulfate and concentrated by evaporation, affording 30 g (54.5% of theory) of 2-(5-isopropyl-5-methyl-4-oxoimidazolin-2-yl)-6-methyl-3-pyridinecarboxylic acid of m.p. 139°–142° C.

EXAMPLE 4

Preparation of 2-(5-isopropyl-5-methyl-4-oxoimidazolin-2-yl)-5-ethyl-3-pyridinecarboxylic acid With stirring, 225 g (2 moles) of potassium tert-butylate are added in portions to a solution of 251 g (1 mole) of diethyl 5-ethyl-2,3-pyridinedicarboxylate and 130 g (1 mole) of 2-amino-2,3-dimethylbutyramide in 1000 ml of dry toluene, whereupon the temperature of the reaction mixture rises to 80° C. When the addition of potassium tert-butylate is complete, the red solution is stirred for 4 hours at 80° C., whereupon the potassium salt of 2-(5-isopropyl-5-methyl-4-oxoimidazolin-2-yl)-5-ethyl-3-pyridinecarboxylic acid precipitates in the form of a dense crystal slurry. The mixture is cooled to room temperatur and, after addition of 1000 ml of water, stirred until the potassium salt is completely dissolved. The organic phase is then separated and the aqueous phase is adjusted to pH 3 by addition of 165 ml of 37% hydrochloric acid. The mixture is subsequently stirred for 1 hour at 0° C. and then filtered, affording 214.4 g (74.2% of theory) of 2-(5-isopropyl-5-methyl-4-oxoimidazolin-2-yl)-5-ethyl-3-pyridinecarboxylic acid of m.p. 171°–173° C.

EXAMPLE 5

Preparation of 2-(5-isopropyl-5-methyl-4-oxoimidazolin-2-yl)-5-bromo-3-pyridinecarboxylic acid With stirring, 20.0 g (0.154 mole) of potassium tert-butylate are added to a solution of 22.0 g (0.073 mole) of diethyl 5-bromo-2,3-pyridinedicarboxylate and 9.5 g (0.073 mole) of 2-amino-2,3-dimethylbutyramide in 250 ml of toluene. The mixture is then stirred for 6 hours at 80° C. and the potassium salt of 2-(5-isopropyl-5-methyl-4-oxoimidazolin-2-yl)-5-bromo-3-pyridinecarboxylic acid is isolated by filtration. The potassium salt is dissolved in water and the pH of the solution is adjusted to 3 by addition of concentrated hydrochloric acid. The mixture is subsequently stirred for 1 hour at 0° C. and filtered, affording 15.5 g (62.4% of theory) of 2-(5-isopropyl-5-methyl-4-oxoimidazolin-2-yl)-5-bromo-3-pyridinecarboxylic acid of m.p. 206° C.–208° C.

EXAMPLE 6

Preparation of 2-(5-isopropyl-5-methyl-4-oxoimidazolin-2-yl)-3-quinolinecarboxylic acid 90.0 g (0.33 mole) of diethyl 2,3-quinolinedicarboxylate and 43.0 g (0.33 mole) of 2-amino-2,3-dimethylisobutyramide are dissolved in 1 liter of toluene. With efficient stirring, 74.0 g (0.66 mole) of potassium tert-butylate are then added, whereupon the temperature rises to 55° C. When the addition of potassium tert-butylate is complete, the reaction mixture is stirred for 5 hours at 90° C., then cooled to room temperature. The potassium salt of 2-(5-isopropyl-5-methyl-4-oxoimidazolin-2-yl)-3-quinolinecarboxylic acid is isolated by filtration and dissolved in 500 ml of water. The pH of the solution is adjusted to 3 by addition of concentrated hydrochloric acid. The crystal suspension is stirred for 1 hour at 0° C. and then filtered, affording 76 g (74% of theory) of 2-(5-isopropyl-5-methyl-4-oxoimidazolin-2-yl)-3-quinolinecarboxylic acid of m.p. 266°–270° C.

In analogous manner, 19.9 g (82.3% of theory) of 2-(5-isopropyl-5-methyl-4-oxoimidazolin-2-yl)-6-chloro-3-quinolinecarboxylic acid of m.p. 234°–237° C. are obtained starting from 21.5 g (0.07 mole) of diethyl 6-chloro-2,3-quinolinedicarboxylate and 9.1 g (0.07 mole) of 2-amino-2,3-dimethylbutyramide and 17.0 g (0.15 mole) of potassium tert-butylate.

What is claimed is:

1. A process for the preparation of a 2-(imidazolin-2-yl)-3-pyridine- or -3-quinolinecarboxylic acid of formula I

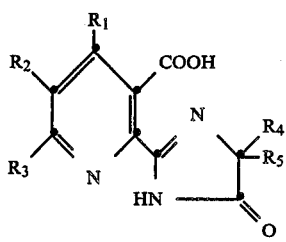

(I)

wherein $R_1$ is hydrogen or $C_1$–$C_4$alkyl, $R_2$ is hydrogen, halogen, $C_1$–$C_4$alkyl, $C_1$–$C_4$hydroxyalkyl, $C_1$–$C_4$alkoxy, phenyl or phenyl-$C_1$–$C_4$-alkyl, or phenyl or phenyl-$C_1$–$C_4$-alkyl, each substituted by one $C_1$–$C_4$alkyl, $C_1$–$C_4$alkoxy or halogen, $R_3$ is hydrogen, $C_1$–$C_4$alkyl, phenyl, phenyl-$C_1$–$C_4$-alkyl, or phenyl or phenyl-$C_1$–$C_4$-alkyl, each substituted by one $C_1$–$C_4$alkyl, $C_1$–$C_4$alkoxy or halogen, $R_2$ and $R_3$ together are 1,3-butadienylene which can be substituted by halogen, $C_1$–$C_4$alkyl, $C_1$–$C_4$alkoxy, $C_1$–$C_4$haloalkyl, $C_1$–$C_4$alkylsulfonyl, nitro, cyano, phenyl, phenoxy, or phenyl or phenoxy, each substituted by one $C_1$–$C_4$alkyl, $C_1$–$C_4$alkoxy or halogen, and $R_4$ and $R_5$ are each independently of the other $C_1$–$C_4$alkyl, which process comprises reacting a 2,3-pyridine- or 2,3-quinolinedicarboxylic acid ester of formula II

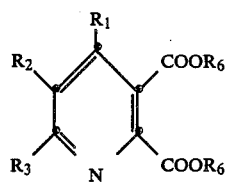

(II)

wherein $R_1$, $R_2$ and $R_3$ are as defined for formula I, and $R_6$ is $C_1$–$C_8$alkyl, phenyl or $C_1$–$C_4$phenylalkyl, with a 2-aminoalkanecarboxamide of formula III

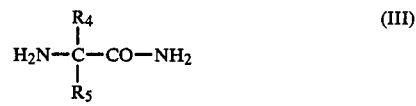

(III)

wherein $R_4$ and $R_5$ are as defined for formula I, in an inert solvent and in the presence of a strong base, at a temperature in the range from room temperature to the reflux temperature of the reaction mixture, dissolving the resultant salt of 2-(imidazolin-2-yl)-3-pyridine- or -3-quinolinecarboxylic acid of formula I in water, adjusting the pH of the aqueous solution to 1.5–4.5, and isolating the free 2-(imidazolin-2-yl)-3-pyridine- or -3-quinolinecarboxylic acid of formula I.

2. A process according to claim 1, wherein the inert solvent is a liquid aromatic hydrocarbon or halogenated hydrocarbon, a $C_1$–$C_{10}$alkanol, tetrahydrofuran, dioxane, acetonitrile, N,N-dimethylformamide or dimethylsulfoxide.

3. A process according to claim 1, wherein the inert solvent is benzene, toluene, chlorobenzene or a xylene.

4. A process according to claim 1, wherein the reaction of a 2,3-pyridine- or 2,3-quinolinedicarboxylic acid ester of formula II with a 2-aminoalkanecarboxamide of formula III is carried out in the presence of an alkali metal hydroxide or alkali metal alcoholate as strong base.

5. A process according to claim 4, wherein 1.5 to 2.5 moles of base are used per mole of 2,3-pyridine- or 2,3-quinolinedicarboxylic acid ester of formula II.

6. A process according to claim 1, wherein the reaction of a 2,3-pyridine- or 2,3-quinolinedicarboxylic acid ester of formula II with a 2-aminoalkanecarboxamide of formula III is carried out in the presence of an alkali metal alcoholate which is derived from a $C_1$–$C_4$alkanol.

7. A process according to claim 6, wherein the reaction of a 2,3-pyridine- or 2,3-quinolinedicarboxylic acid ester of formula II with a 2-aminoalkanecarboxamide of formula III is carried out in the presence of potassium tert-butylate.

8. A process according to claim 1, wherein the reaction of a 2,3-pyridine- or 2,3-quinolinedicarboxylic acid ester of formula II with a 2-aminoalkanecarboxamide of formula III is carried out in the temperature range from 50° to 90° C.

9. A process according to claim 1, wherein the salt of a 2-(imidazolin-2-yl)-3-pyridine- or -3-quinolinecarboxylic acid of formula I, obtained by reacting a 2,3-pyridine- or 2,3-quinolinedicarboxylic acid ester of formula II with a 2-aminoalkanecarboxamide of formula III, is isolated by filtration from the reaction mixture and converted into an aqueous solution by dissolving said salt in water.

10. A process according to claim 1, wherein the salt of a 2-(imidazolin-2-yl)-3-pyridine- or -3-quinolinecarboxylic acid of formula I, obtained by reacting a 2,3-pyridine- or 2,3-quinolinedicarboxylic acid ester of formula II with a 2-aminoalkanecarboxamide of formula III, is converted into an aqueous solution by direct addition of water to the reaction mixture.

11. A process according to claim 1, wherein the 2-(imidazolin-2-yl)-3-pyridine- or -3-quinolinecarboxylic acid of formula I is recovered from the aqueous solution of its salt by adjusting the pH of the aqueous solution to 3–4 by addition of hydrochloric acid or sulfuric acid.

12. A process for the preparation of a 2-(imidazolin-2-yl)-3-pyridine- or -3-quinolinecarboxylic acid of formula I, wherein $R_1$ is hydrogen, $R_2$ and $R_3$ are each independently of the other hydrogen, $C_1$–$C_2$alkyl, $C_1$–$C_2$haloalkyl, $C_1$–$C_2$alkoxy or halogen, and $R_2$ and $R_3$ together are 1,3-butadienylene, and $R_4$ and $R_5$ are each independently of the other $C_1$–$C_3$alkyl.

13. A process for the preparation of a 2-(imidazolin-2-yl)-3-pyridine- or -3-quinolinecarboxylic acid of formula I, wherein $R_1$ is hydrogen, $R_2$ and $R_3$ are each independently of the other $C_1$–$C_2$alkyl or halogen and together are 1,3-butadienylene, $R_4$ is methyl and $R_5$ is isopropyl.

14. A process according to claim 1, which comprises carrying out the reaction of a 2,3-pyridine- or 2,3-quinolinedicarboxylic acid ester of formula II with a 2-aminoalkanecarboxamide of formula III in the presence of 1.5 to 2.5 moles of an alkali metal alcoholate per mole of diester of formula II, at a temperature in the range from 50° to 90° C., and in a liquid aromatic hydrocarbon or halogenated hydrocarbon, converting the isolated salt of the resultant 2-(imidazolin-2-yl)-3-pyridine- or -3-quinolinecarboxylic acid of formula I into an aqueous solution by addition of water, separating the organic phase, adjusting the pH of the aqueous phase to 3–4 by addition of aqueous hydrochloric acid or aqueous sulfuric acid, and isolating the free 2-(imidazolin-2-yl)-3-pyridine or -3-quinolinecarboxylic acid of formula I.

15. A process according to claim 1, wherein 1.5 to 2.5 moles of base are used per mole of 2,3-pyridine- or 2,3-quinolinedicarboxylic acid ester of formula II.

* * * * *